United States Patent [19]

Katsuki et al.

[11] Patent Number: 5,352,814
[45] Date of Patent: Oct. 4, 1994

[54] ASYMMETRIC EPOXIDATION REACTION

[75] Inventors: Tsutomu Katsuki; Naoki Hosoya; Akira Hatayama, all of Fukuoka, Japan

[73] Assignee: Nissan Chemical Industries, Ltd., Tokyo, Japan

[21] Appl. No.: 933,785

[22] Filed: Aug. 24, 1992

[30] Foreign Application Priority Data

Aug. 30, 1991 [JP] Japan ................................. 3-220087
Feb. 25, 1992 [JP] Japan ................................. 4-037466
Jul. 31, 1992 [JP] Japan ................................. 4-205374

[51] Int. Cl.$^5$ .............................................. C07F 3/02
[52] U.S. Cl. ...................................... 556/50; 548/126
[58] Field of Search .......................................... 556/50

[56] References Cited

U.S. PATENT DOCUMENTS 4,900,752  2/1990  Seto et al. ........................ 514/364
5,097,037  3/1992  Matsumoto et al. ............. 548/126

FOREIGN PATENT DOCUMENTS 0327127     8/1989   European Pat. Off. .
0409165     1/1991   European Pat. Off. .
52-91866    8/1977   Japan .
2-49788     2/1990   Japan .
3-141286    6/1991   Japan .
WO91/14694 10/1991   PCT Int'l Appl. .
1548221     7/1979   United Kingdom .
1548222     7/1979   United Kingdom .

OTHER PUBLICATIONS

Hatayama, Synlett 409, 1992.
Hosoya, Synlett 691, 1991.
World Patents Index of "Berwent" (1993).
J. Med. Chem. 1984, 27, pp. 1127-1131.
Tetrahedron Letters, vol. 32, No. 8, pp. 1055-1058 (1991).
Tetrahedron: Asymmetry, vol. 2, pp. 481-494, 1991.
Tetrahedron Letters, vol. 31, No. 50, pp. 7345-7348, 1990.

*Primary Examiner*—Robert Gerstl
*Attorney, Agent, or Firm*—Oliff & Berridge

[57] ABSTRACT

A process for producing an optically active benzopyran compound of the formula [I] or [II]:

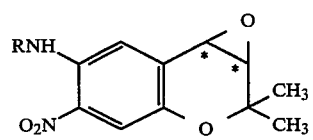

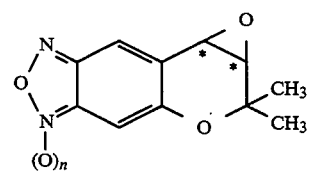

in which an olefin compound of the formula [V] or [VI]:

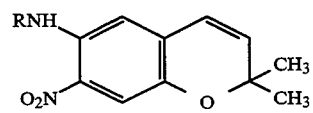

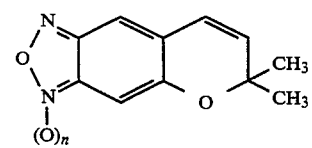

is subjected to asymmetric epoxidation reaction, using, as a catalyst, an optically active manganese complex of the formula [III] or [IV]:

(Abstract continued on next page.)

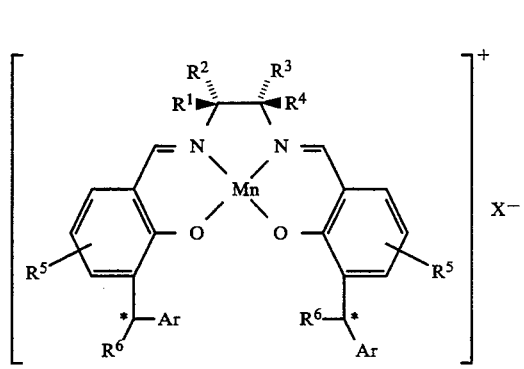
[III]
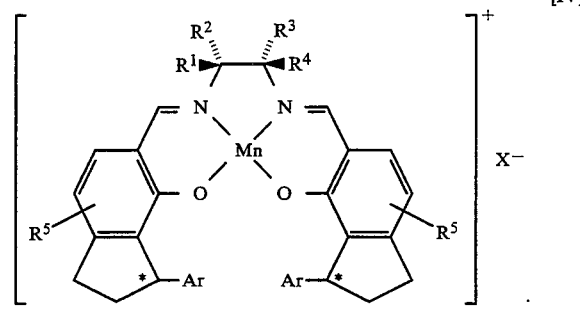
[IV]
1 Claim, No Drawings

ASYMMETRIC EPOXIDATION REACTION

BACKGROUND OF THE INVENTION

1. Field of the Invention

The present invention relates to a benzopyran compound, which is an important intermediate in synthesis of optically active pyranobenzoxadiazole compounds useful for the treatment of hypertension, asthma, etc., and to a process for producing the same.

2. Description of the Prior Art

Pyranobenzoxadiazole compounds of the formula [VII]:

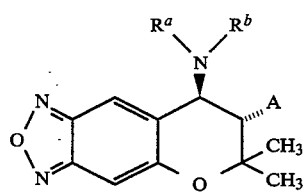

wherein A represents a hydroxyl group or $OC(O)CH_{3-n}X_n$, in which X is fluorine atom, chlorine atom, bromine atom, methyl group or methoxy group and n is 0 or an integer of 1 to 3;

when $R^a$ represents a hydrogen atom, $R^b$ represents a hydrogen atom, $C(Z)CH_{3-n}X_n$ or $C(Z)NHCH_{3-n}X_n$ in which Z represents oxygen atom or sulfur atom and n has the same meaning as defined above; and when $R^a$ does not represent a hydrogen atom, $R^a$ and $R^b$ together form $(CH_2)_{m-1}C(Z)$ in which m is an integer of 4 or 5 and Z has the same meaning as defined above, $(CH_2)_{m-2}NHC(Z)$ or $(CH_2)_{m-2}OC(Z)$ in which Z and m have the same meanings as defined above, are described in Japanese Patent Laid-Open No. Hei 2-49788 (49788/1990), EP-A-0 327 127 and U.S. Pat. No. 4,900,752. The compounds exert intense vasodilatory and hypotensive activities, and thus are expected to be useful as a medicine for treating hypertension, angina pectoris, arrhythmia, cerebral circulation disorder and asthma.

There are two kinds of optical isomers for the compounds of the formula [VII] since the compounds have asymmetric carbon atoms at the 3- and 4-positions of the pyran ring, and only one antipode exhibits excellent activity as a medicine, as shown in Japanese Patent Laid-Open No. Hei 3-141286 (141286/1991), EP-A-0 409 165 and U.S. Pat. No. 5,097,037. However, since the antipode is synthesized from an optically active compound [VIII] (an optically active compound showing dextrorotation in ethanol) as a raw material in accordance with Scheme 1. The production thereof has shown economical problems. (see Japanese Patent Laid-Open No. Hei 3-141286, EP-A-0 409 165 and U.S. Pat. No. 5,097,037).

Scheme 1

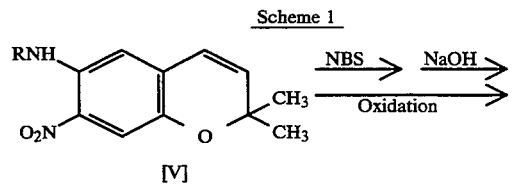

-continued
Scheme 1

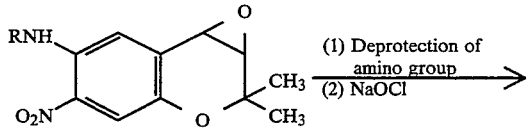

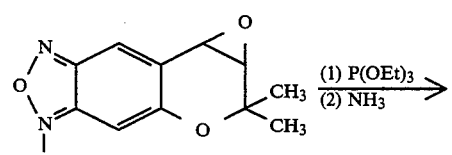

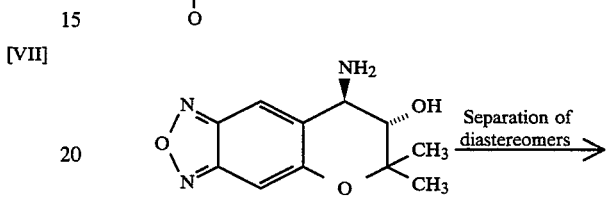

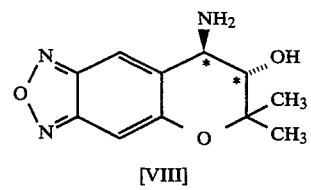

NBS:N-Bromosuccinimide

SUMMARY OF THE INVENTION

Thus, the present invention is to establish a process for producing optically active pyranobenzoxadiazole compounds [VIII] in an effective and economical manner, wherein optically active isomers of Compound [I]:

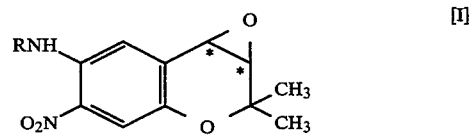

in which R represents hydrogen atom or an amino-protecting group and the absolute configuration of carbon atom which is marked with asterisks means R or S or optically active isomers of Compound [II]:

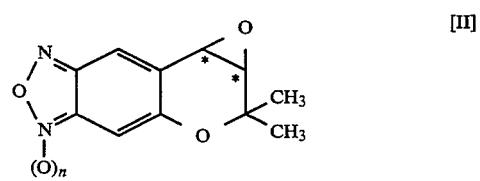

in which n is 0 or an integer of 1 and the absolute configuration of carbon atom means R or S, are synthesized in an enantioselective manner by utilizing asymmetric synthesis.

An object of the present invention is to provide a process for producing an intermediate compound of a therapy of hypertension.

DESCRIPTION OF THE PREFERRED EMBODIMENTS

The present inventors extensively investigated asymmetric epoxidation reaction (Reaction 1 and Reaction 2 as shown below) of olefin compounds [V]:

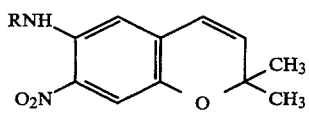

in which R represents hydrogen atom or an amino-protecting group or olefin compounds [VI]:

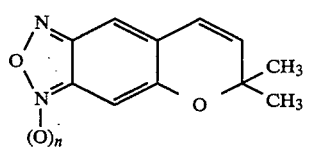

in which n is 0 or an integer of 1 so as to obtain the optically active benzopyran compounds [I]:

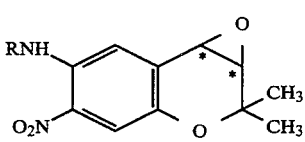

in which R has the same meaning as defined above and the absolute configuration of carbon atom which is marked with asterisks means R or S or optically active benzopyran compounds [II]:

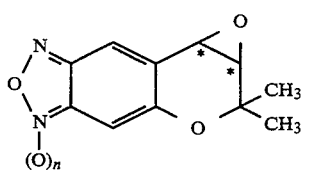

in which n is 0 or an integer of 1 and the absolute configuration of carbon atom which is marked with asterisks means R or S. As a result, they found out that the intended compounds can be obtained at the highest asymmetric yields by using, as asymmetric catalyst, an optically active manganese complex of the formula [III] wherein $R^1$, $R^2$, $R^3$, $R^4$ and $R^5$ can be same or different and represent hydrogen atom or straight chain or branched alkyl group having 1 to 4 carbon atoms, or phenyl group which is unsubstituted or substituted by one or more substituents arbitrarily selected from one or more groups of fluorine atom, chlorine atom, bromine atom, straight chain or branched alkyl group having 1 to 4 carbon atoms and straight chain or branched alkoxyl group having 1 to 4 carbon atoms, $R^6$ represents straight chain or branched alkyl group having 1 to 4 carbon with proviso that when $R^6$ represents ethyl group, either one of $R^1$ and $R^2$ and either one of $R^3$ and $R^4$ do not simultaneously represent phenyl group, Ar represents phenyl group which is unsubstituted or substituted by one or more substituents arbitrarily selected from one or more groups of fluorine atom, chlorine atom, bromine atom, straight chain or branched alkyl group having 1 to 4 carbon atoms and straight chain or branched alkoxyl group having 1 to 4 carbon atoms, and the absolute configuration shown by the asterisks means R or S and $X^-$ represents a counter anion or an optically active manganese complex of the formula [IV] wherein $R^1$, $R^2$, $R^3$, $R^4$, $R^5$, $X^-$ and the asterisks are defined above.

Reaction 1

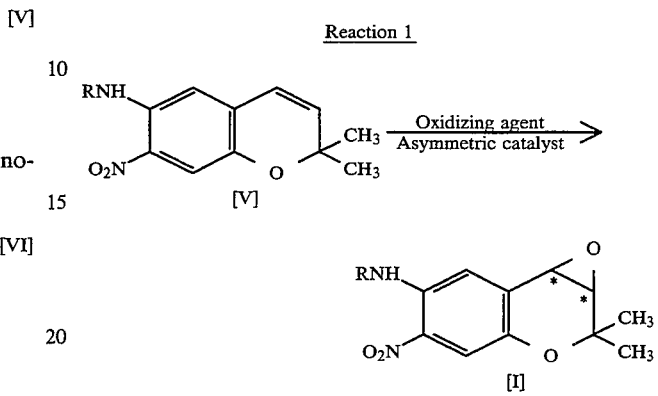

Reaction 2

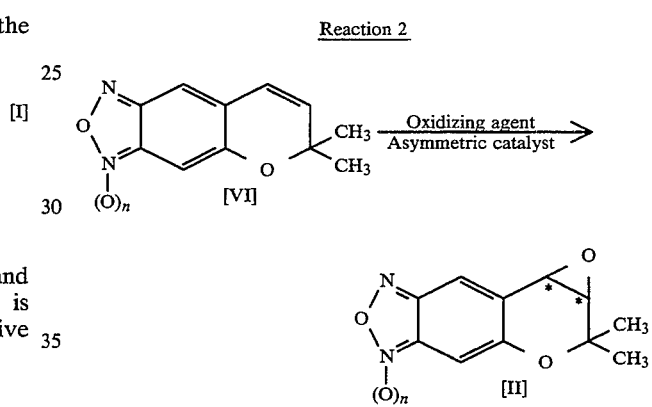

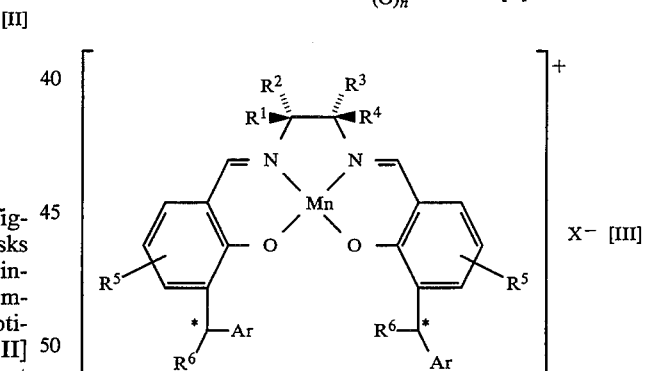

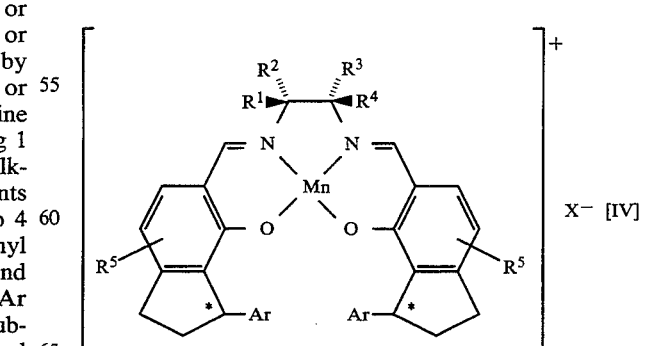

R which is a substituent of the compound [I] represents hydrogen atom or an amino-protecting group.

Examples of the protecting group include acyl group such as acetyl group, propionyl group, benzoyl group, alkoxycarbonyl group such as methoxycarbonyl group, ethoxycarbonyl group and tertiary butoxycarbonyl group, and tosyl group and benzyl group. Preferable examples of R are acetyl group and tertiary butoxycarbonyl group.

The olefin compound [V] as a starting material is known and can be readily synthesized according to the methods described in Japanese Patent Laid-Open No. Sho 52-91866 (91866/1977) and British Patents No. 1,548,221 and No. 1,548,222. The olefin compound [VI] can be readily synthesized according to the methods described in Japanese Patent Laid-open No. Hei 2-49788 (49788/1990), EP-A-0 327 127 and U.S. Pat. No. 4,900,752, by using the compound [V] as a starting material.

Examples of $R^1$, $R^2$, $R^3$, $R^4$ and $R^5$ which are substituents of the optically active manganese complexes [III] and [IV] include hydrogen atom, methyl group, ethyl group or straight chain or branched alkyl group having 3 to 4 carbon atoms such as normal-propyl group, isopropyl group, normal-butyl group, isobutyl group, secondary butyl group and tertiary butyl group, or phenyl group which is unsubstituted or substituted by one or more substituents arbitrarily selected from one or more groups of fluorine atom, chlorine atom, bromine atom, methyl group, ethyl group, normal-propyl group, isopropyl group, normal-butyl group, isobutyl group, secondary butyl group and tertiary butyl group, methoxy group, ethoxy group, normal-propoxy group, isopropoxy group, normal- butoxy group, isobutoxy group, secondary butoxy group and tertiary butoxy group, preferably, hydrogen atom, ethyl group and phenyl group.

Examples of $R^6$ include methyl group, ethyl group, normal-propyl group, isopropyl group, normal-butyl group, isobutyl group, secondary butyl group and tertiary butyl group, preferably, methyl group and ethyl group.

Examples of Ar include fluorine atom, chlorine atom, bromine a tom, methyl group, ethyl group, phenyl group which is unsubstituted or substituted by one or more substituents arbitrarily selected from one or more groups of normal-propyl group, isopropyl group, normal-butyl group, isobutyl group, secondary butyl group and tertiary butyl group, methoxy group, ethoxy group, normal -propoxy group, isopropoxy group, normal butoxy group, isobutoxy group, secondary butoxy group, tertiary butoxy group; preferably, phenyl group.

The optically active manganese complexes [III] and [IV] can form salt together with various kinds of counter anion ($X^-$) as manganese which is a metal center can be monovalent to pentavalent oxidized state. Examples of the counter anion include monovalent $OH^-$, $F^-$, $Cl^-$, $Br^-$, $I^-$, $CH_3CO_2^-$, $PF_6^-$ and $ClO_4^-$ ions, divalent $CO_3^{2-}$ and $SO_4^{2-}$, trivalent $PO_4^{3-}$ ion. All of these salts can be used as asymmetric catalyst of the present invention.

The following is the typical synthesis examples of the optically active manganese complexes [III] and [IV].

The Scheme 2 shows a case of the complex of the formula [III] wherein $R^1=R^2=H$, $R^3=R^4=R^5=R^6=CH_3$ and Ar=Ph (phenyl group). Namely, 4 -methyl -salicylic acid is (a) esterificated with methyl orthoformate and then subjected to (b) cinnamylation under basic conditions, (c) Claisen rearrangement in the presence of calcium carbonate, (d) catalytic reduction and then to (e) hydrolysis of ester to give a racemic carboxylic acid. Subsequently, the racetalc carboxylic acid is (f) optically separated by using brucine as an optically resolving agent, (g) reacted with lithium aluminum hydride (LAH) to reduce the carboxylic group of the acid into an alcohol, and then (h) oxidized the alcohol with 2,3-dichloro-5,6-dicyano-1,4-benzoquinone (DDQ) to give optically active 4-methyl-3-(1-phenylpropyl )salicylaldehyde, which can be converted into the optically active compound [III] in accordance with the method described in Example 1 or 2 ( see Tetrahedron Letters , Vol. 32, No. 8 , 1055–1058 (1991)). In the method described in Examples 1 or 2, the above-mentioned aldehyde is stirred in ethanol together with manganese acetate-tetrahydrate and then reacted with 1,2-diamino-2-methylpropane. After distilling off the solvent, the residue is recrystallized from hexane-acetone to obtain the desired product.

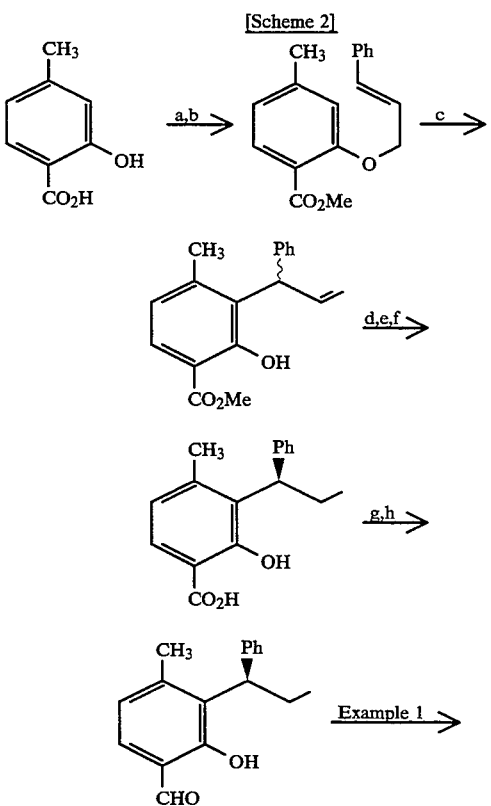

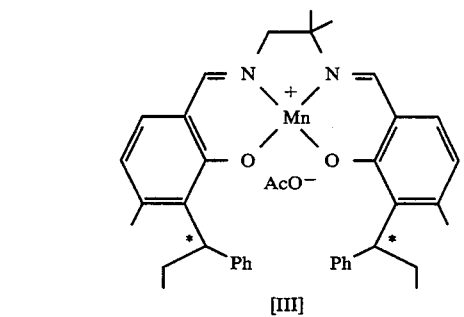

(a) $(MeO)_3CH$, 120° C., 2 days;
(b) NaH; $PhCH=CHCH_2Br$; Solvent, DMF; Yield, 77% (overall yield in 2 steps)
(c) $CaCO_3$; 170–180° C.; 1 day; Yield, 73%;
(d) $H_2$—Pd/C; Solvent, AcOEt; Yield, 100%:
(e) NaOH(5M); Solvent, EtOH; followed by HCl treatment;

-continued
[Scheme 2]
Yield, 100%;
(f) (−)-brucine 2H₂O; Recrystallized from acetone (thrice); followed by HCl treatment; Yield 22%;
(g) LAH; Solvent, THF; Yield, 99%;
(h) DDQ; Solvent, AcOEt; Yield, 86%.
(Me = CH₃, Ph = C₆H₅, Ac = CH₃CO, Et = C₂H₅)

The Scheme 3 shows a case of the complex of the formula [III] wherein $R^6$=CH₃ and Ar=Ph Namely, 2-hydroxyacetophenone which is substituted with $R^5$ is (a) alkylated by phenyllithium in the presence of cerium chloride and is (b) hydrogenerated by Pd-C under the acidic conditions, and (c) under acidic conditions, tetrahydropyranyl group (THP) is introduced and (d) formyl group is introduced via ortholithiation and tetrahydropyranyl group is (e) deprotected under acidic conditions, and the obtained salicylaldehyde derivative is (f) reacted with (−)-methylchloroformate and the obtained diastereomer is separated by recrystallization. Then, (g) by hydrolyzing methylcarbonate by alkali, the optically active 3- (1-phenylethyl)-salicylaldehyde substituted with $R^5$ is prepared. In accordance with the method described in Example 2, the optically active compound [III] is prepared from the salicylaldehyde.

with 3-chloropropionic acid chloride to obtain ester, (b) the Fries rearrangement and Friedel Crafts alkylation are simultaneously conducted by AlCl3, (c) alkylation is made by phenylmagnesium bromide, (d) hydroxyindane derivative obtained by Pd-C hydrogenation under basic conditions is (e) reacted with (−)-methylchloroformate to obtain diastereomer. The diastereomer is separated by recrystallization. Then, (f) menthylcarbonate is alkalihydrolyzed and (g) under acidic conditions, phenol is protected as tetrahydropyrane. After (h) formyl group is introduced via ortholithiation, (i) tetrahydropyranyl group is deprotected under basic conditions to prepare an optically active 6-formyl-7-hydroxy-1-phenylindane substituted with $R^5$. In accordance with the method described in Example 3, the optically active compound [IV ] can be obtained from the phenylindane.

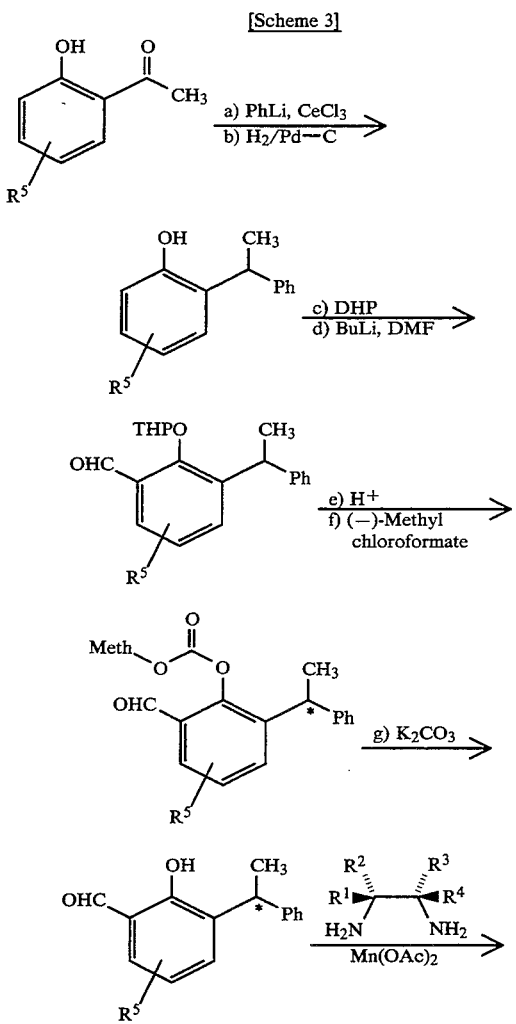

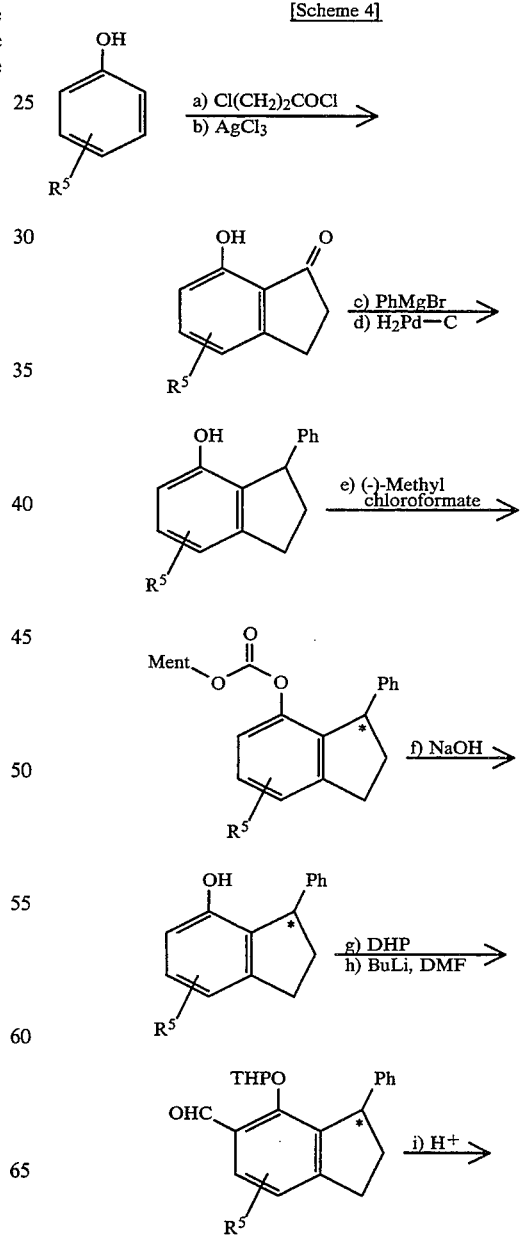

An optically active (salen)manganese complex [IV] can be synthesized by the routes shown in the Scheme 4 . Namely, (a) Phenol substituted with $R^5$ is reacted -continued
[Scheme 4]

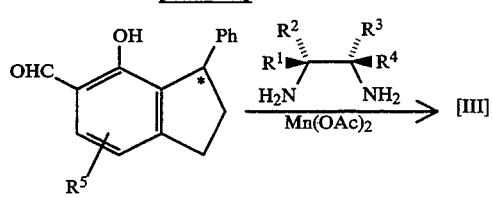

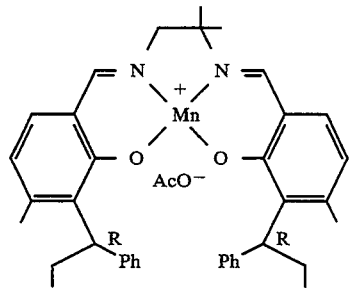

Next, the method (Reaction Scheme 1 or 2) for preparing optically active benzopyrane compound [I] or [II] is explained.

Asymmetrical catalyst, namely, optically active manganese complex [III] or [IV], is used at a concentration in the range of from 0.1 mol % to 100 mol %, preferably from 1 mol % to 5 mol %, based on the mole of the compound of the formula [V] or VII. Examples of usable oxidizing agents include iodosobenzene, sodium hypochlorite, and the like. When iodosobenzene is used as the oxidizing agents, it is usually used in the range of from 1 to 10 equivalents, preferably 1 to 3 equivalents, based on the compound [V] or [VI]. When sodium hypochlorite is used as the oxidizing agents, it is usually used in the range of from 1 to 100 equivalents, preferably, in the range of from 3 to 30 equivalents.

As a medium for the reaction, there can be used water, acetonitrile, dichloromethane, dichloroethane and a mixture thereof. Especially, when sodium hypochlorite is used as the oxidizing agent, it may be preferable to use two-phase system such as water and dichloromethane. Also, it can co-exist a component having coordination ability with the manganese complex such as pyridine N-oxide, lutidine N-oxide or 2-methylimidazole in the reaction system. There is no particular limitation on the quantity of the components to be used.

The reaction is ordinarily carried out at a temperature in the range of $-20°$ C. to $50°$ C., preferably, $-20°$ C. to $25°$ C.

After the completion of the reaction, the organic solvent is distilled off under reduced pressure to concentrate the reaction solution and only separated and purified by using a silica gel column chromatography to isolate the desired optically active compound [I] or [II]. The optical purity of [I] or [II] can be analyzed by optically active liquid chromatographic column (using, e.g., Chiralcel OJ mfd. by Daicel Chemical Industries, Ltd., under conditions as shown in Example).

The present invention will further be illustrated by examples.

EXAMPLES

Example 1

Synthesis of Optically Active Manganese Complex [III ($R^1=R^2=H$, $R^3=R^4=R^5=CH_3$, $R^6=CH_2CH_3$ and Ar=Ph)]

(1) R-isomer (catalyst A)

To 2.8 ml of ethanol were added 97.0 mg (0.381 mmol) of (R)-4-methyl-3-(1-phenylpropyl)salicylaldehyde (a compound known to the literature, Tetrahedron Letters, Vol. 32, No. 8, 1055–1058 (1991)) and 47.1 mg (0.192 mmol) of manganese acetatetetrahydrate, and the resulting mixture was stirred for twenty minutes. Subsequently, 20 µl (0.193 mmol) of 1,2-diamino-2-methylpropane was added thereto, and the resulting mixture was stirred for twenty hours.

Thereafter, the reaction mixture was concentrated under reduced pressure, and the residue obtained was recrystallized from hexane-acetone to obtain 77.5 mg (yield=56%) of the titled compound (catalyst A).
IR: 2956, 1615, 1585, 1525, 1381, 1291, 745, 694, 639 cm$^{-1}$
Elementary Analysis:
Calcd. for $C_{40}H_{45}Mn_1N_2O_4$·AcOH: C, 68.84; H, 6.73; N, 3.82 Found: C, 68.62; H, 6.59; N, 3.81
(2) S-isomer The titled compound was synthesized in a similar manner described above, by using (S)-4-methyl-3-(1-phenylpropyl)salcylaldehyde as a starting material. IR: 2956, 1615, 1585, 1525, 1381, 1291, 745, 694, 639 cm$^{-1}$ Example 2

Synthesis of Optically Active Manganese Complex [III ($R^1=R^3=H$, $R^2=R^4=Ph$, $R^5=R^6=CH_3$ and Ar=Ph)]

(1) R-isomer (catalyst B)
To 0.36 ml of degassed acetonitrile (dried on MS4A) were added 43.3 mg (0.180 mmol) of (R)-4-methyl-3-(1-phenylethyl) salicylaldehyde and 19.2 mg (0.090 mmol) of (R, R)-1,2-diphenylethylenediamine and stirred for twenty minutes. The mixture was added with 0.36 ml of solution of 22.1 mg (0.090 of manganese acetate-tetrahydrate in acetonitrile and stirred for four hours. To the mixture was poured 0.36 ml of solution of 29.9 mg (0.090 mmol) of ferricenium hexafluorophosphate ($Cp_2FePF_6$) in acetonitrile and was stirred for fifteen hours. Thereafter, the residue obtained by concentration under reduced pressure was washed thrice with 2 ml of hexane to obtain the titled compound (catalyst B). (yield: 54%)
(2) S-isomer (catalyst C)
The titled compound (catalyst C) was obtained in the similar manner described above by using (S,S)-1,2-diphenylethylenediamine instead of (R,R)-1,2-diphenylethylenediamine.
Example 3

Synthesis of Optically Active Manganese Complex [IV ($R^{d1}=R^3=H$, $R^2=R^4=Ph$, $R^5=H$ and Ar=Ph)]

(1) R-isomer (catalyst D)

To 0.6 ml of ethanol were added 45.3 mg (0.190 mmol) of (R)-6-formyl-7-hydroxy-1-phenylindane and 23.3 mg (0,095 mmol) of manganese acetate-tetrahydrate and stired for twenty minutes. The mixture was added 20.2 mg (0.095 mmol) of (R,R)-1,2-diphenylethylenediamine and further stirred for twenty hours. Thereafter, the residue obtained by concentration under reduced pressure was recrystallized from hexane-dichloromethane to obtain the titled compound (catalyst D). (yield: 43%)

(2) S-isomer (catalyst E)

The titled compound (catalyst E) was obtained in the similar manner described above by using (S,S)-1,2-diphenylethylenediamine instead of (R,R)-1,2-diphenylethylenediamine.

Example 4 (Asymmetric Epoxidation Reaction)

(1) Reaction Example which uses iodosobenzene as an oxidizing agent

To 1.4 ml of acetonitrile were added 0.068 mmol of the compound [V] or [VI], $1.36 \times 10^{-3}$ mmol of the optically active (salen)manganese complex [III] or [IV] and 0.136 mmol of iodosobenzene and stirred for twenty four hours at room temperature or −20° C. After the completion of the reaction, the reaction mixture was concentrated under reduced pressure and the residue was subjected to a silica gel chromatography (eluent: hexane-ethyl acetate=4:1→1:1) to obtain the intended optically active epoxy compound [I] or [II].

The result is shown in Table 1.

TABLE 1

Asymmetric epoxidation using iodosobenzene as an oxidizing agent

| Substrate | Catalyst | Temperature | Chemical Yield (%) | Optical Yield (% E.e.) | Optical Rotation in CHCl₃ |
|---|---|---|---|---|---|
| 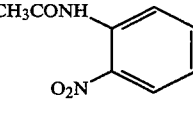 | A | r.t. | 73 | 63 | (+) |
| | B | r.t. | 94 | 88 | (+) |
| | B | −20°C. | 82 | 90 | (+) |
| | C | r.t. | 70 | 67 | (−) |
| | D | r.t. | 92 | 49 | (+) |
| | E | r.t. | 72 | 70 | (−) |
| 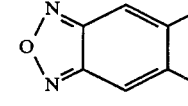 | B | r.t. | 76 | 86 | (−) |
| | B | −20° C. | 70 | 87 | (−) |
| 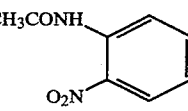 | B | r.t. | 83 | 87 | (−) |
| | B | −20° C. | 77 | 89 | (−) | r.t.: room temperature (2) Reaction Example which uses sodium hypochlorite as an oxidizing agent To 0.5 ml of dichloromethane was added 0,076 mmol of the compound [V] or [VI], $1.52 \times 10^{-3}$ mmol of the optically active (salen)manganese complex [III] or [IV], 0.45 ml ( adjusted to pH=11.3) of 0.55 M sodium hypochlorite (co-existence with 0.075 ml of 0.05M sodium phosphate (II)) and $1.52 \times 10^{-3}$ mmol of lutidine N-oxide and stirred for twenty four hours at 0° C. The mixture was extracted with dichloromethane. The extracted substance dried and concentrated under reduced pressure was subjected to a column chromatography (eluate: hexane-ethyl acetate=4:1→1:1) to isolate the intended optically active epoxy compound [I] or [II].

The result is shown in Table 2.

TABLE 2

Asymmetric epoxidation using sodium hypochlorite as an oxidizing agent

| Substrate | Catalyst | Temperature | Chemical Yield (%) | Optical Yield (% E.e.) | Optical Rotation in CHCl₃ |
|---|---|---|---|---|---|
| 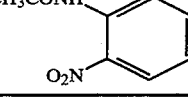 | B | 0° C. | 33 | 92 | (+) |

Reference Example

The asymmetric epoxidation reaction of the compound [V] was conducted under the same conditions of the Example 4-(1) by using the following catalyst F described in Tetrahedron: Asymmetry (vol. 2, pp. 481–494, 1991). The result was that only 19% of optical purity was obtained. (see Table 3).

TABLE 3

(Reference).
Asymmetric epoxidation using iodosobenzene as an oxidizing agent

| Substrate | Catalyst | Temperature | Chemical Yield (%) | Optical Yield (% E.e.) | Optical Rotation in CHCl₃ |
|---|---|---|---|---|---|

TABLE 3-continued (Reference).
Asymmetric epoxidation using iodosobenzene as an oxidizing agent

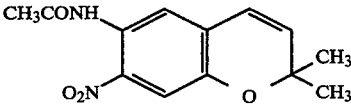
| | F | r.t. | 90 | 19 | (+) | r.t.: room temperature
Catalyst F

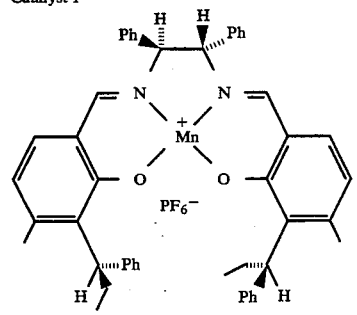

(Determination of Optical Purity)

Measured by high performance liquid chromatography using an optically active liquid chromatographic column ( Chiralcell OJ, 250 mm×4.6 mm mfd. by Daicel Chemical Industries , Ltd.).

Eluent: hexane- isopropanol=2:1
Flow rate: 0.5 ml/min.
Detected wavelength: 254 nm

What is claimed is:

1. An optically active manganese complex of the formula:

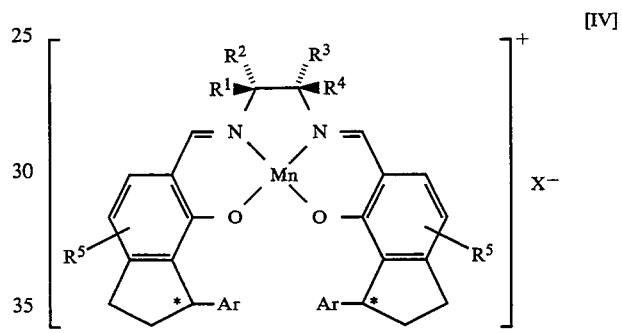

wherein $R^1$, $R^2$, $R^3$, $R^4$ and $R^5$ are same or different and represent hydrogen atom or straight chain or branched alkyl group having 1 to 4 carbon atoms , or phenyl group which is unsubstituted or substituted by one or more substituents arbitrarily selected from one or more groups of fluorine atom, chlorine atom, bromine atom, straight chain or branched alkyl group having 1 to 4 carbon atoms and straight chain or branched alkoxyl group having 1 to 4 carbon atoms, Ar represents phenyl group which is unsubstituted or substituted by one or more substituents arbitrarily selected from one or more groups of fluorine atom, chlorine atom, bromine atom, straight chain or branched alkyl group having 1 to 4 carbon atoms and straight chain or branched alkoxyl group having 1 to 4 carbon atoms, and the absolute configuration of the carbon atom shown by asterisks means R or S and $X^-$ represents a counter anion.

* * * * *